(12) United States Patent
Mohammed et al.

(10) Patent No.: US 12,029,710 B2
(45) Date of Patent: *Jul. 9, 2024

(54) EPHEDRINE COMPOSITIONS AND METHODS

(71) Applicant: Nevakar Injectables Inc., Bridgewater, NJ (US)

(72) Inventors: Irfan Ali Mohammed, Piscataway, NJ (US); Tushar Hingorani, Bridgewater, NJ (US); Kumaresh Soppimath, Skillman, NJ (US)

(73) Assignee: Nevakar Injectables Inc., Bridgewater, NJ (US)

(*) Notice: Subject to any disclaimer, the term of this patent is extended or adjusted under 35 U.S.C. 154(b) by 77 days.

This patent is subject to a terminal disclaimer.

(21) Appl. No.: 17/960,343

(22) Filed: Oct. 5, 2022

(65) Prior Publication Data
US 2023/0039936 A1 Feb. 9, 2023

Related U.S. Application Data

(60) Division of application No. 17/096,822, filed on Nov. 12, 2020, now Pat. No. 11,491,121, which is a continuation of application No. 16/749,378, filed on Jan. 22, 2020, now Pat. No. 10,869,845.

(51) Int. Cl.
| | | |
|---|---|---|
| A61K 31/137 | (2006.01) | |
| A61K 47/02 | (2006.01) | |
| A61K 47/12 | (2006.01) | |

(52) U.S. Cl.
CPC ............ *A61K 31/137* (2013.01); *A61K 47/02* (2013.01); *A61K 47/12* (2013.01)

(58) Field of Classification Search
CPC ...... A61K 31/137; A61K 9/0019; A61K 9/08; A61K 47/02; A61K 47/12
See application file for complete search history.

(56) References Cited

U.S. PATENT DOCUMENTS

| | | |
|---|---|---|
| 10,869,845 B1 | 12/2020 | Mohammed |
| 11,090,278 B2 | 8/2021 | Ahmed |
| 2005/0021092 A1 | 1/2005 | Yun |
| 2010/0216667 A1 | 8/2010 | Meyer et al. |
| 2020/0360309 A1* | 11/2020 | Ahmed .................... A61K 9/08 |
| 2021/0393552 A1 | 12/2021 | Ahmed |
| 2022/0110892 A1 | 4/2022 | Ahmed |

FOREIGN PATENT DOCUMENTS

| | | |
|---|---|---|
| CN | 102688184 A | 9/2012 |
| CN | 102688253 A | 9/2012 |

OTHER PUBLICATIONS

"Ephedrine sulfate injection," United States Pharmacopeia (41st rev.) / National Formulary (36th ed.) (2018), 6 pgs.
"AKOVAZ (ephedrine sulfate injection, USP) for intravenous use," FDA Prescribing Information (Apr. 2016), 8 pgs.
Australian Government Department of Health, "Australian Public Assessment Report for Ephedrine Hydrochloride" (Jun. 2017), 34 pgs.
Australian Government Department of Health, "Australian Public Assessment Report for Ephedrine Hydrochloride" (Oct. 2017), 34 pgs.
Bastin et al., "Salt Selection and Optimisation Procedures for Pharmaceutical New Chemical Entities," 4 Organic Process Research & Development 427-435 (2000), 9 pgs.
Bellefleur, et al., "Use of Ephedrine prefilled syringes reduces anesthesia costs," 28 Ann Fr Anesth. 211-14 (2009), 4 pgs.
Bendsen et al., "Number of germ cells and somatic cells in human fetal testes during the first weeks after sex differentiation," 18:1 Human Reproduction 13-18, 13 (2003), 6 pgs.
Bicker et al., "Enantiomeric impurity profiling in ephedrine samples by enantioselective capillary electrochromatography," 24 Electrophoresis 2532-2542 (2003), 11 pgs.
Diven, et al., "Extending Shelf Life Just Makes Sense," 90(11) Mayo Clin. Proc. 1471-74 (2015), 4 pgs.
Donahue, "Are Prefilled Syringes Worth it?," Outpatient Surgery Magazine (2017) (available at https://www.aorn.org/outpatient-surgery/the-magazine/article/2017-january-are-prefilled-syringes-worth-it), 7 pgs.
Ephedrine Hydrochloride 3 mg/ml Solution for Injection in Prefilled syringe, Electronic Medicines Compendium (first authorization 2010) (available at https://www.medicines.org.uk/emc/product/5354/smpc#gref), 10 pgs.
FDA, "Guidance for Industry: Sterile Drug Products Produced by Aseptic Processing—Current Good Manufacturing Practice" (Aug. 2003), 63 pgs.
Griffiths, et al., "The stability of ready-to-use (RTU) ephedrine hydrochloride in polypropylene syringes for use in maternal hypotension," 11(5) Eur. J. Hosp. Pharm. 107-10 (2005), 4 pgs.
European Medicines Agency, "ICH Topic Q3B (R2): Impurities in New Drug Products" (Jun. 2006), 14 pgs.
Lee et al., "Large-Scale Aspects of Salt Formation: Processing of Intermediates and Final Products," in Handbook of Pharmaceutical Salts: Properties, Selection, and Use (Stahl and Wermuth, eds., 2002), 20 pgs.
Lyon, et al., "Stability Profiles of Drug Products Extended beyond Labeled Expiration Dates," 95(7) J. Pharm. Sci. 1549-60 (2006), 12 pgs.
Ma et al., "Pharmacological Effects of Ephedrine Alkaloids on Human α1- and α2-Adrenergic Receptor Subtypes," 322:1 JPET 214-221 (2007), 9 pgs.
Morgan, "The role of vasopressers in the management of hypotension induced by spinal and epidural anaesthesia," 41:5 Can J Anaesth 404-413 (1994), 10 pgs.

(Continued)

*Primary Examiner* — Sarah Pihonak
(74) *Attorney, Agent, or Firm* — Mayer Brown LLP

(57) ABSTRACT

Disclosed herein are storage-stable ephedrine single-phase solution compositions, comprising 4 mg/mL to 6 mg/mL of ephedrine, a pH adjuster comprising acetic acid, and water, wherein the composition has a pH between 4.5 and 5.0; and wherein the pH drift of the composition is less than 0.5 after storage over at least two months at 25° C. and 60% relative humidity. Also disclosed herein are methods of making and using the same.

15 Claims, No Drawings

(56) References Cited

OTHER PUBLICATIONS

Serajuddin, "Salt Formation to Improve Drug Solubility," 59 Advanced Drug Delivery Reviews 603-616 (2007), 14 pgs.
Efedrin Stragen (ephedrine hydrochloride) Public Assessment Report, Läkemedelsverket Medical Products Agency (2011), 8 pgs.
Task Force on Sterile Pharmaceutical Products Produced by Terminal Sterilization, "Guidance on the Manufacture of Sterile Pharmaceutical Products Produced by Terminal Sterilization" (2012), 74 pgs.
Torlot, "Coloured drug labels and prefilled syringes—another mistake waiting to happen," 68 Anaesthesia 308-09 (2013), 2 pgs.
Trissel, "Trissel's Stability of Compounded Formulations" (5th ed. 2012), 4 pgs.
World Health Organization, "WHO good manufacturing practices for sterile pharmaceutical products" (2011), 24 pgs.
Wu et al., "Determination of enantiomeric purity of ephedrine and pseudoephedrine by high-performance liquid chromatography with dual optical rotation/UV absorbance detection," 8:4 J. Pharmaceutical & Biomedical Analysis 353-364 (1990), 8 pgs.
"2.9.19 Particulate Contamination: Sub-Visible Particles," European Pharmacopoeia (9th ed. 2016), 6 pgs.
"5.1 General Texts on Sterility", European Pharmacopoeia (9th ed. 2016), 26 pgs.
Center for Drug Evaluation and Research, "Approval Package for Application No. 208289Orig1s000 (AKOVAZ Injection, 50 mg/mL)" (Apr. 2016), 184 pgs.
United States Food & Drug Administration, Sterile Drug Products Produced by Aseptic Processing—Current Good Manufacturing Practice, Guidance for Industry, Sep. 2004.
Jeanne Moldenhauer, Validation of Moist Heat Sterilization, Encyclopedia of Pharmaceutical Science and Technology, 2012, fourth edition, vol. 1, pp. 1-11.
Sheldon T. Bradshaw, Esq., Suitability Petition Pursuant to Section 505(j)(2)(C) of the FDC Act for Ephedrine Sulfate Injection, USP, 50 mg/10 mL (5 mg/mL), Apr. 2, 2018, 28 pages.
The United States Pharmacopeia USP 34, NF 29, Bacterial Endotoxins Test, May 1, 2011, pp. 78-81, vol. 1.
The United States Pharmacopeia USP 34, NF 29, General Requirements for Tests and Assays, May 1, 2011, pp. 33-38, vol. 1.
The United States Pharmacopeia USP 34, NF 29, Particulate Matter in Injections, May 1, 2011, pp. 326-328, vol. 1.
The United States Pharmacopeia USP 32, NF 27, Ephedrine, May 1, 2009, pp. 2258-2260, vol. 2.
"Ephedrine sulfate injection," The International Pharmacopoeia, 2016, Sixth Edition, 1 page.
Aguettant Ltd, "Ephedrine Hydrochloride 3 mg/ml Solution for Injection in Pre-filled Syringe," Oct. 2015; 10 pgs.
Aguettant Ltd., "Ephedrine Hydrochloride 3 mg/ml Solution for Injection in Pre-filled Syringe," Jul. 19, 2019, pp. 1-7. Retrieved from the Internet pp. 1, 5, 7.
Aguettant, prescribing information for ephedrine HCl, 2015, pp. 1-2.
Akers, Michael J., "Sterile Drug Products: Formulation, Packaging, Manufacturing, and Quality," 2010 Informa Healthcare, London, UK; 517 pgs.
AKOVAZ Prescribing Information, 2016, FDA, pp. 1-8.
Black et al., "Structure, Solubility, Screening, and Synthesis of Molecular Salts," Journal of Pharmaceutical Sciences, May 2007; 96(5):1053-1068.
Delatte, Marcus S., Ph.D., Reviewer, "Center for Drug Evaluation and Research, Pharmacology Review(s)," Jun. 30, 2015; 48 pgs.
Gad, Shayne Cox, "Pharmaceutical Manufacturing Guidebook: Production and Processes," 2008, John Wiley & Sons, Inc., Hoboken, New Jersey; 1386 pgs.
International Search Report and Written Opinion for PCT/US2020/017875 dated Oct. 15, 2020; 8 pgs.
Niazi, Sarfaraz K., "Handbook of Pharmaceutical Manufacturing Formulations: Sterile Products, vol. 6," 2004, CRC Press LLC, Boca Raton, Florida; 363 pgs.
Sacha, et al., "Practical fundamentals of glass, rubber, and plastic sterile packaging systems," Pharmaceutical Development and Technology, 2010; 15(1):6-34.
Sacha, et al., "Pre-filled syringes: a review of the history, manufacturing and challenges," Pharm Dev Technol., 2015; 20(1):1-11.
U.S. Department of Health and Human Services, Food and Drug Administration, "Guidance for Industry: Sterile Drug Products Produced by Aseptic Processing—Current Good Manufacturing Practice," Sep. 2004, Pharmaceutical CGMPs; 63 pgs.

* cited by examiner

EPHEDRINE COMPOSITIONS AND METHODS

This application claims priority to our co-pending and allowed US application having Ser. No. 17/096,822, filed Nov. 12, 2020, which is a continuation of U.S. Pat. No. 10,869,845, having Ser. No. 16/749,378, and which was filed Jan. 22, 2020.

FIELD OF THE INVENTION

The field of the invention is pharmaceutical formulations, such as premixed formulations of ephedrine, or a pharmaceutically acceptable salt thereof, that are patient ready for injectable use.

BACKGROUND

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Ephedrine is an alpha- and beta-adrenergic agonist and a norepinephrine-releasing agent. The chemical name of ephedrine sulfate is (1R,2S)-(−)-2-methylamine-1-phenyl-propan-1-ol sulfate, and the molecular weight is 428.5 g/mol. Its structural formula is depicted below:

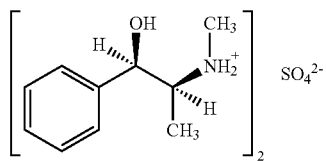

Ephedrine sulfate is freely soluble in water and ethanol, very slightly soluble in chloroform, and practically insoluble in ether.

A commercially-available, FDA-approved ephedrine sulfate formulation, AKOVAZ™ (ephedrine sulfate injection), is a clear, colorless, sterile solution for intravenous injection. AKOVAZ™ must be diluted with normal saline or 5% dextrose in water, before administration as an intravenous bolus to achieve the desired concentration. The recommended dosages for the treatment of clinically important hypotension in the setting of anesthesia is an initial dose of 5 to 10 mg administered by intravenous bolus. Additional boluses may be administered as needed, not to exceed a total dosage of 50 mg.

AKOVAZ™ is available in the market at a concentration of 50 mg/mL. Before administration to a patient, medical personnel have to dilute AKOVAZ™ to about 5 mg/mL. This dilution process takes time, introduces human error, and is difficult to do under emergency circumstances. Furthermore, the dilution process causes a risk of contamination, as well as a risk for overdose.

On the other hand, FDA-approved, diluted, ready to use ephedrine injection formulations are not available in the market. Diluted solutions of ephedrine are not pH stable, and are known to have pH drifts of up to 2 pH units. However, under the current FDA guidelines, the pH of Ephedrine sulfate injection formulations should be between 4.5 and 7.0. In fact, the FDA directs that upon dilution, the pH of the solution should be checked and/or adjusted to be in the range of 4.5 and 7.0.

Thus, there remains a need in the art for new Ephedrine sulfate injection formulations that are ready to use for injection in patients, are storage stable and pH stable, and which do not significantly drift in pH over time.

SUMMARY OF THE INVENTION

The inventive subject matter is directed to premixed pharmaceutical compositions of ephedrine, or a pharmaceutically acceptable salt thereof, that are formulated for administration to a patient, without the need to reconstitute or dilute the composition prior to administration. Thus, the compositions of the present disclosure are formulated as a premixed composition comprising ephedrine, or a pharmaceutically acceptable salt thereof.

In one aspect of the inventive subject matter, disclosed herein is a storage-stable ephedrine single-phase solution composition, comprising: 4 mg/mL to 6 mg/mL of ephedrine; a pH adjuster comprising acetic acid; and wherein the initial adjusted pH of the composition is between 4.5 and 5.0; and wherein the pH drift of the composition is less than 0.5 after storage over at least two months at 25° C. and 60% relative humidity. Preferably, the initial pH of the composition is between 4.50 and 4.65, or between 4.65 and 4.80, or between 4.80 and 4.90, or between 4.90 and 5.0. The pH of the composition is adjusted with a pH adjuster, which is preferably acetic acid and/or sodium hydroxide. Preferably, the ephedrine disclosed in the compositions herein comprises ephedrine sulfate. Furthermore, the compositions and formulations disclosed herein is contemplated to contain about 5% or less total impurities after storage for 6 months at 25° C. and 60% relative humidity as determined by HPLC.

In some embodiments, the composition may further comprise a tonicity agent. The tonicity agent may be a pharmaceutically acceptable salt, such as sodium chloride. The concentration of the sodium chloride may be at a concentration of 1 mg/mL to 30 mg/mL. The tonicity agent may also comprise a saccharide, such as lactose and/or dextrose.

In some embodiments, the composition may also comprise a buffer. The buffer, when present, has a concentration of equal to or less than 60 mM, or preferably equal to or less than 50 mM. The buffer may comprise monobasic and dibasic sodium phosphate.

Additionally, the composition may also comprise a chelator. The chelator is selected from the group consisting of a bicarboxylic acid, a tricarboxylic acid, and an aminopolycarboxylic acid.

Furthermore, the composition may also comprise a viscosity modifier. The viscosity modifier may be modified cellulose, such as hydroxyethyl cellulose, a hydroxypropyl cellulose, or a hydroxypropyl methylcellulose.

In some preferred embodiments, the compositions of the disclosure are substantially free of a preservative. In other embodiments, the compositions and formulations of the disclosure may contain a preservative.

The storage stability of the compositions disclosed herein may be increased by storing the composition in an inert plastic vial, such as a polypropylene vial.

In another aspect of the inventive subject matter, disclosed herein is a method of increasing storage stability of ephedrine in a single-phase solution formulation, comprising: formulating an aqueous solution comprising 4 mg/mL to 6 mg/mL of ephredine; adjusting the pH of the solution to between 4.5 and 5.0 with a pH adjuster comprising acetic acid; and wherein the formulation is formulated such that after storage over at least two months at 25° C. and 60% relative humidity, the pH drift of the formulation is less than 0.5.

Preferably, the method further comprises a step of sterilizing the formulation. The step of sterilizing may comprise sterile filtration or autoclaving.

The formulation may be packaged in a single-dose container or a multi-dose container.

In another aspect of the inventive subject matter, the inventors have disclosed a pharmaceutical kit for administering an injectable formulation at room temperature, comprising: an ephedrine formulation having 4 mg/mL to 6 mg/mL of ephredine, a pH adjuster comprising acetic acid, and water; wherein the formulation has a pH between 4.5 and 5.0; and wherein the pH drift of the formulation is less than 0.5 after storage over at least two months at 25° C. and 60% relative humidity; and instructions for using the formulation.

Various objects, features, aspects and advantages of the inventive subject matter will become more apparent from the following detailed description of preferred embodiments.

DETAILED DESCRIPTION OF THE INVENTION

The present disclosure is based in part on the inventor's finding of a premixed ephedrine formulation that does not require reconstitution or dilution prior to administration to a patient, remains substantially pH stable and active after prolonged storage. Such premixed formulations therefore avoid the cost, inconvenience, and risk of contamination or overdose that can be associated with reconstituting or diluting a concentrated ephedrine formulation prior to administration to a patient.

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

A pharmaceutically acceptable salt of ephedrine can include inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, and salicylic acid. Preferably, the ephedrine in the premixed pharmaceutical compositions is in the form of a pharmaceutically acceptable salt. More preferably, the salt is ephedrine sulfate.

The terms "premixed" or "ready-to-use" as used herein refers to a pharmaceutical formulation that does not require reconstitution or dilution prior to administration to a patient. For example, in contrast to non-premixed formulations of ephedrine, the premixed compositions provided herein are suitable for administration to a patient without dilution by, for example, a clinician, hospital personnel, caretaker, patient or any other individual.

In certain embodiments, the compositions of the present disclosure can be formulated as a "single use dosage," which refers to a premixed composition that is disposed within a sealed container or vessel as a one dose per container or vessel formulation. Alternatively, compositions of the present disclosure can be formulated as a "multiple use dosage," which refers to a premixed composition that is disposed within a sealed container or vessel as a multiple dose per container or vessel formulation, i.e., two or more doses, preferably between two and four doses, and most preferably two doses.

According to the present disclosure, a "subject" or "patient" is a human, a non-human mammal or a non-human animal. Although the animal subject is preferably a human, the compounds and compositions of the disclosure have application in veterinary medicine as well, e.g., for the treatment of domesticated species such as canine, feline, and various other pets; farm animal species such as bovine, equine, ovine, caprine, porcine, etc.; wild animals, e.g., in the wild or in a zoological garden; and avian species, such as chickens, turkeys, quail, songbirds, etc.

The term "pharmaceutically acceptable," when used in connection with the pharmaceutical compositions of the disclosure, refers to molecular entities and compositions that are physiologically tolerable and do not typically produce untoward reactions when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, dispersing agent or vehicle with which the compound is administered. Pharmaceutically acceptable carriers can be liquids, such as water and oils. For example, water, aqueous solutions, saline solutions, Ringer's lactate, aqueous dextrose or glycerol solutions can be employed as carriers, particularly for injectable solutions. Suitable pharmaceutical carriers are described in, for example, "Remington's Pharmaceutical Sciences" by Philip P. Gerbino, 21st Edition (or previous editions).

The term "about" as used herein contemplates what is ordinarily meant in the art, and includes an acceptable range for a particular value as determined by a skilled artisan in the art. This, in turn, may depend on how the value is determined, or it may depend on the result to be achieved. For example, used in the context of chemical compositions, the term "about" allows for a degree of variation inherent in the methods utilized for measuring the chemical compounds, and/or also allows for a degree of variation that produces the same or similar result in term of desired effectiveness.

The term "pH stable" means that the composition has a pH drift of less than 1.0 for an indicated length of time, under the stated stability conditions. A pH stable composition is contemplated to have a pH drift of less than 1.0, or more preferably pH drift of less than 0.9, or more preferably pH drift of less than 0.8, or more preferably pH drift of less than 0.7, or more preferably pH drift of less than 0.6, or more preferably pH drift of less than 0.5, or more preferably pH drift of less than 0.4, or more preferably pH drift of less than 0.3, or more preferably pH drift of less than 0.2, or most preferably pH drift of less than 0.1 for an indicated length of time, under the stated stability conditions. The length of time is contemplated to be 6 months, more preferably 8 months, more preferably 10 months, and most preferably 12 months. In preferred embodiments, the pH stable compositions contemplated herein has a pH drift of less than 0.5 after storage for 6 months at 25° C. and 60% relative humidity The term "acid" as used herein refers to a chemical substance that lowers the pH (increases the hydrogen concentration) when added to an aqueous solution. An acid can be inorganic or organic. The term "organic" acid as used herein refers to any acid the radical of which is a carbon derivative or a compound in which a hydrocarbon radical is united to COOH (a carboxylic acid) or to $SO_3H$ (a sulfonic acid). The term "inorganic" acid as used herein refers to any acid containing no hydrocarbon moiety. Acids can be "monobasic" wherein they have but one replaceable hydrogen atom and yield only one series of salts (e.g., HCl) or "polybasic" wherein they contain two or more hydrogen atoms which may be neutralized by alkalies and replaced by organic radicals.

The acids as used herein may be an inorganic or organic acid. Organic acids, i.e. acids that include a hydrocarbon moiety) for use with the subject invention include, but are not limited to, any organic acid of one to six (C1 to C6) carbons in length. Organic acids include, but are not limited to formic, acetic, propionic, maleic, butanoic, valeric, hexanoic, phenolic, cyclopentanecarboxylic, benzoic acids, and the like. For an organic acid, the acid can be in concentrated form, or can be diluted. Suitable inorganic acids include halogen acids, oxy acids and mixtures. Specific inorganic acids of interest include, but are not limited to, hydrochloric, nitric, sulfuric, phosphoric, hydroboric, hydrobromic, carbonic and hydroiotic acids. For an inorganic acid, the acid can be a concentrated acid, or can be diluted. Upon dilution, the concentration of an inorganic acid will generally be from about 10 N to about 0.01 N, preferably between 5 N to 0.1 N.

Preferably, the compositions disclosed herein are single phase solutions. The term "single phase solution" as used herein refers to a liquid homogeneous system that is both physically and chemically uniform throughout. Preferably, after addition of ephedrine to the composition, the liquid components of the composition or carrier are fully miscible, and the solid components if any, are either dissolved or suspended in the composition. In one embodiment, for example, single phase solution may be determined by differential scanning calorimetry (DSC). The DSC scan should show one peak indicative of a single phase. By "substantially a single phase" is meant that the composition or carrier after addition of ephedrine is primarily or essentially a single phase as explained above, but may also have present a small amount of material which is capable of forming or may form a separate phase amounting to less than about 5% of the composition or carrier after the addition of ephedrine, preferably less than about 3%, and more preferably less than about 1%.

Currently, diluted ready to use solutions of ephedrine are not FDA approved. Diluted solutions of ephedrine are known to have pH drifts of up to 2 pH units. The inventors of the present disclosure have surprisingly found a formulation of ephedrine that is substantially pH stable, and that is in a ready to use concentration without the need of any additional dilution prior to use. The compositions and formulations disclosed by the inventors comprise an aqueous storage-stable single-phase solution composition, comprising ephedrine and a pH adjuster. The pH of this formulation, once adjusted to between 4.5 and 5.0, remains stable at that pH (having a drift less than 0.5) after storage over at least two months at 25° C. and 60% relative humidity.

In one embodiment, the inventors have disclosed a storage-stable, sterile ephedrine ready-to-use solution composition, comprising: about 5 mg/mL of ephedrine; about 9 mg/mL of sodium chloride; a pH adjuster comprising acetic acid; and water, wherein the initial adjusted pH of the composition is in the range of 4.6 to 4.8; wherein the pH drift of the composition is less than 0.5 after storage for 6 months at 25° C. and 60% relative humidity; and wherein the composition contains about 5% or less total impurities after storage for 6 months at 25° C. and 60% relative humidity as determined by HPLC. The term "initial adjusted pH" as used herein refers to the pH initial adjusted to when the formulation is being made. Once the formulation is made, and the pH is set to the initial adjusted pH, it is contemplated that the composition will have a pH drift of less than 0.5 for up to 6 months or more preferably up to one year of storage at room temperature.

AKOVAZ' is sold at a concentration of 50 mg/mL and is usually diluted to 5 mg/mL just prior to injection. Dilute ephedrine (such as at a concentration of 5 mg/mL) result in a pH drift outside the FDA recommended pH of 4.5-7.0. Of course, a buffer could be used to stabilize the pH; however, it was found that presence of buffers may affect the long-term stability and efficacy of ephedrine. Ready to use ephedrine injection solutions are not currently FDA approved. The inventors surprisingly found that when the initial adjusted pH of ephedrine (5 mg/mL) is between 4.6-4.8, and when the solution has sodium chloride in a range from 5 mg/mL to 15 mg/mL (preferably about 9 mg/mL), and when the initial pH is adjusted with acetic acid, then the ready to use ephedrine sulfate solution, with a concentration of 5 mg/mL, has a stable pH and does not degrade over a long period of time.

Therefore, contemplated ephedrine formulations of the inventive subject matter can be advantageously provided in a ready-to-use format that avoids the inconvenience associated with diluting concentrated ephedrine formulations into diluents prior to administration. Thus, the ready-to-use formulations also eliminate microbial contamination risks and/or calculation errors associated with dilution. Most typically, contemplated formulations will be available in a range of concentrations commonly required by medical practitioners for treatment of hypotension. Consequently, ephedrine will typically be present in formulations in an amount of equal or less than 3 mg/mL, or in an amount of equal or less than 4 mg/mL, or in an amount of equal or less than 5 mg/mL. For example, the ephedrine or a pharmaceutically acceptable salt thereof may be present in the injectable composition in an amount of between 3 mg/mL and 4 mg/mL, between 4 mg/mL and 5 mg/mL, or between 5 mg/mL and 6 mg/mL, or between 6 mg/mL and 7 mg/mL, or between 7 mg/mL and 8 mg/mL, or between 8 mg/mL and 9 mg/mL, or between 9 mg/mL and 10 mg/mL. As will be readily appreciated, ephedrine for the preparation of contemplated formulations may be ephedrine or any suitable pharmaceutically acceptable salt thereof, including mineral salts and organic salts (e.g., sulfate). Similarly, where desired, the ephedrine may also be used in any suitable prodrug form.

In certain embodiments, the premixed ephedrine composition is a liquid comprising ephedrine, or a pharmaceutically acceptable salt thereof, in water at a concentration of between about 2.5 mg/mL and about 20 mg/mL, preferably about 5 mg/mL to about 10 mg/mL. In other embodiments, the premixed ephedrine composition is a liquid comprising ephedrine, or a pharmaceutically acceptable salt thereof, in water at a concentration of about 5 mg/mL or about 10 mg/mL. In other embodiments, the premixed ephedrine composition is a liquid comprising ephedrine, or a pharmaceutically acceptable salt thereof, in water at a dose of between about 5 mg and about 10 mg, preferably about 5 mg or about 10 mg.

For example, in one exemplary embodiment, the concentration of ephedrine in contemplated formulations is from about 2 mg/mL to about 4 mg/mL; or from about 3 mg/mL to about 5 mg/mL; or from about 4 mg/mL to about 6 mg/mL; or from about 5 mg/mL to about 7 mg/mL; or from about 6 mg/mL to about 8 mg/mL; or from about 7 mg/mL to about 9 mg/mL; or from about 8 mg/mL to about 10 mg/mL; or from about 9 mg/mL to about 11 mg/mL; or from about 10 mg/mL to about 12 mg/mL; or from about 11 mg/mL to about 13 mg/mL; or from about 12 mg/mL to about 14 mg/mL; or from about 13 mg/mL to about 15 mg/mL; or from about 14 mg/mL to about 16 mg/mL; or from about 15 mg/mL to about 17 mg/mL; or from about 16 mg/mL to about 18 mg/mL; or from about 17 mg/mL to about 19 mg/mL; or from about 18 mg/mL to about 20 mg/mL. Most preferably, the concentration of ephedrine in compositions and formulations disclosed herein is about 5 mg/mL.

The compositions and formulations disclosed herein are contemplated to have a substantially stable pH over an extended period of time. Preferably, the pH drift is less than 2.0 pH units after storage over at least 2 months, preferably at least 6 months, more preferably at least 12 months, even more preferably at least 18 months, and most preferably at least 24 months, at 25° C. and 60% relative humidity. More preferably, the pH drift is less than 1.5 pH units after storage over at least 2 months, preferably at least 6 months, more preferably at least 12 months, more preferably at least 18 months, and most preferably at least 24 months, at 25° C. and 60% relative humidity. Even more preferably, the pH drift is less than 1.0 pH units after storage over at least 2 months, preferably at least 6 months, more preferably at least 12 months, even more preferably at least 18 months, and most preferably at least 24 months, at 25° C. and 60% relative humidity. Even more preferably, the pH drift is less than 0.8 pH units after storage over at least 2 months, preferably at least 6 months, more preferably at least 12 months, even more preferably at least 18 months, and most preferably at least 24 months, at 25° C. and 60% relative humidity. Most preferably, the pH drift is less than 0.5 pH units after storage over at least 2 months, preferably at least 6 months, more preferably at least 12 months, even more preferably at least 18 months, and most preferably at least 24 months, at 25° C. and 60% relative humidity.

In other embodiments, the premixed ephedrine composition comprises ephedrine, or a pharmaceutically acceptable salt thereof, mixed or dissolved in a sodium chloride saline solution.

In certain embodiments, the premixed ephedrine composition is disposed within a sealed container or vessel. In certain embodiments, the premixed ephedrine composition is disposed within a sealed container as a total volume of about 5 mL to about 100 mL.

In certain embodiments, the premixed ephedrine composition comprises ephedrine, or a pharmaceutically acceptable salt thereof, in water at a concentration of between about 2.5 mg/mL and about 20 mg/mL, preferably about 5 mg/mL to about 10 mg/mL, and sodium chloride at a concentration of between about 1 mg/mL and about 30 mg/mL, preferably about 5 mg/mL to about 20 mg/mL.

In other embodiments, the premixed ephedrine composition comprises ephedrine, or a pharmaceutically acceptable salt thereof, in water at a concentration of about 5 mg/mL or about 10 mg/mL, and sodium chloride at a concentration of about 9 mg/mL.

In certain embodiments, the premixed ephedrine composition comprises ephedrine, or a pharmaceutically acceptable salt thereof, water and one or more pH adjusters, wherein initial pH is in the range of 4.5 to 5.0, and the product is pH stable for at least 6, 12, 18 or 24 months at 25±2° C. and 60±5% relative humidity. Preferably, the one or more pH adjusters comprises glacial acetic acid and/or sodium hydroxide. Optionally, the composition comprises sodium chloride, Ringer's lactate, or dextrose solution. Other acids besides acetic acid are also contemplated for adjusting the pH of the compositions and formulations disclosed herein.

In certain embodiments, the compositions disclosed herein are for administration to a subject for treatment of clinically important hypotension occurring in the setting of anesthesia.

Suitable buffers are generally buffers that stabilize the pH of the contemplated liquid formulations in a pH range of about 4.5 to 5.0, for example about 4.6 to 4.8, or about 4.7. While not limiting to the inventive subject matter, the buffer strength is typically relatively low, for example, equal or less than 100 mM, equal or less than 75 mM, equal or less than 60 mM, equal or less than 50 mM, or between 5 mM and 50 mM (e.g., 10 mM, 20 mM, 30 mM, 40 mM).

Of course, it should be appreciated that there are many types of buffer systems and buffers known in the art, and all of those are deemed suitable for use herein, including buffer systems comprising an acid and a salt of the acid, a first and a second salt (e.g., monobasic and dibasic salt), and amphoteric buffer molecules. For example, suitable buffer systems with an acid and a salt of the acid include citric acid/sodium citrate buffers, ethanoic acid/sodium ethanoate buffers, boric acid/sodium borate, while suitable buffers having a first and a second salt include monobasic sodium phosphate/dibasic sodium phosphate, or monobasic sodium phosphate/sodium citrate, etc. Similarly, suitable amphoteric buffer molecules include HEPES, MOPS, PIPES, MES, etc.

Moreover, in further contemplated aspects, the formulation will also include one or more chelating agents, and particularly metal ion chelators. For example, suitable chelators include various bicarboxylic acids, tricarboxylic acids, and aminopolycarboxylic acids such as ethylenediaminetetraacetic acid (EDTA), ethylene glycol-bis(β-aminoethyl ether)-N,N,N',N'-tetraacetic acid (EGTA), and penta(carboxymethyl)diethylenetriamine (DTPA), and salts and hydrates thereof.

Consequently, suitable chelating agents include monomeric polyacids such as EDTA, cyclohexanediamine tetraacetic acid (CDTA), hydroxyethylethylenediamine triacetic acid (HEDTA), diethylenetriamine pentaacetic acid (DTPA), dimercaptopropane sulfonic acid (DMPS), dimercaptosuccmic acid (DMSA), aminotrimethylene phosphonic acid (ATPA), citric acid, ophthalmologically acceptable salts thereof, and combinations of any of the foregoing. Further suitable chelating agents include pyrophosphates, tripolyphosphates, and, hexametaphosphates, chelating antibiotics such as chloroquine and tetracycline, nitrogen-containing chelating agent containing two or more chelating nitrogen atoms within an imino group or in an aromatic ring (e.g., diimines, 2,2'-bipyridines, etc.), and various polyamines such as cyclam (1,4,7,11-tetraazacyclotetradecane), N—(C1-C30 alkyl)-substituted cyclams (e.g., hexadecyclam, tetramethylhexadecylcyclam), diethylenetriamine (DETA), spermine, diethylnorspermine (DENSPM), diethylhomo-spermine (DEHOP), and deferoxamine (N'-[5-[[4-[[5-(acetylhydroxyamino)pentyl]amino]-1,4-dioxobutyl]hydroxy-amino]pentyl]-N'-(5-aminopentyl)-N-hydroxybutanediamide; also known as desferrioxamine B and DFO).

With respect to suitable salts it is contemplated that the salt is a pharmaceutically acceptable salt that can be used to increase tonicity. Therefore, pharmaceutically acceptable salts are contemplated, and especially NaCl, at a concentration of at least 0.2 wt %, or at least 0.4 wt %, or at least 0.5 wt %, or at least 0.7 wt %. For example, suitable salt concentrations are between 0.2 wt % and 1.1 wt %, 0.4 wt % and 0.9 wt %, or 0.3 wt % and 0.7 wt %. Depending on the particular salt concentration, additional tonicity agents may be added and suitable tonicity agents include glycerol, thioglycerol, mannitol, lactose, and dextrose. The amount of tonicity adjusting agent used can be adjusted to obtain osmolality of the formulations in the range of 260 to 340 mOsm/kg. An osmometer can be used to check and adjust the amount of tonicity adjusting agent to be added to obtain the desired osmolality.

As contemplated formulations are used as an injectable formulation, it is generally preferred that the formulation also includes a viscosity modifier to adjust the viscosity of the formulation to a dynamic viscosity of between 5 and 50 cP (centipoise), and more preferably between 10 and 40 cP, and most preferably between 10 to 30 cP. While there are numerous viscosity modifiers known in the art such as various polymers, glycerol, and polysaccharidic polymers (all of which are contemplated herein), especially preferred viscosity modifiers include cellulosic viscosity modifiers. For example, particularly preferred cellulosic viscosity modifiers include modified and unmodified hydroxyethyl cellulose, hydroxypropyl cellulose, and hydroxypropyl methylcellulose.

As will be readily appreciated, the exact quantity of the viscosity modifier may vary depending on the type of modifier used and desired final viscosity. For example, where the viscosity modifier is a cellulosic modifier and the final viscosity should be between 1 and 30 cP, suitable quantities of the modifier will typically be in the range of 0.5 wt % (+/−0.1 wt %) of the ephedrine composition. The person of ordinary skill will be readily able to adjust the viscosity to a desired measure using viscometers (e.g., rotational, vibration, etc.) well known in the art.

In exemplary embodiments, suitable concentrations of the viscosity modifier in contemplated injectable formulations may be any value less than 5% (w/w). For example, suitable concentrations of the viscosity modifier include 0.01% to 4.99% (w/w); or 0.05% to 4.50% (w/w), 0.10% to 3.50% (w/w), 0.15% to 3.00% (w/w), 0.20% to 2.50% (w/w), 0.21% to 2.20% (w/w), 0.22% to 2.10% (w/w), 0.23% to 2.00% (w/w), 0.24% to 1.90% (w/w); 0.25% to 1.80% (w/w), 0.26% to 1.70% (w/w), 0.27% to 1.60% (w/w), 0.28% to 1.50% (w/w), 0.29% to 1.40% (w/w), 0.30% to 1.30% (w/w), 0.31% to 1.2% (w/w), 0.32% to 1.10% (w/w), 0.33% to 1.00% (w/w), 0.34% to 0.90% (w/w); 0.35% to 0.80% (w/w), 0.36% to 0.75% (w/w), 0.37% to 0.70% (w/w), 0.38% to 0.69% (w/w), 0.39% to 0.68% (w/w), 0.40% to 0.67% (w/w), 0.41% to 0.66% (w/w), 0.42% to 0.65% (w/w), 0.43% to 0.64% (w/w), 0.44% to 0.63% (w/w), 0.45% to 0.62% (w/w), 0.45% to 0.61% (w/w), 0.45% to 0.60% (w/w), 0.45% to 0.59% (w/w), 0.45% to 0.58% (w/w), 0.45% to 0.57% (w/w), 0.45% to 0.56% (w/w), 0.45% to 0.55% (w/w), 0.46% to 0.54% (w/w), 0.47% to 0.53% (w/w), 0.48% to 0.52% (w/w) or 0.49% to 0.51% (w/w).

Therefore, appropriate concentrations of the viscosity modifier in contemplated injectable formulations include 0.01%, 0.02%, 0.03%, 0.04%, 0.05%, 0.06%, 0.07%, 0.08%, 0.09%, 0.10%, 0.11%, 0.12%, 0.13%, 0.14%, 0.15%, 0.16%, 0.17%, 0.18%, 0.19%, 0.20%, 0.21%, 0.22%, 0.23%, 0.24%, 0.25%, 0.26%, 0.27%, 0.28%, 0.29%, 0.30%, 0.31%, 0.32%, 0.33%, 0.34%, 0.35%, 0.36%, 0.37%, 0.38%, 0.39%, 0.40%, 0.41%, 0.42%, 0.43%, 0.44%, 0.45%, 0.46%, 0.47%, 0.48%, 0.49%, 0.50%, 0.51%, 0.52%, 0.53%, 0.54%, 0.55%, 0.56%, 0.57%, 0.58%, 0.59%, 0.60%, 0.61%, 0.62%, 0.63%, 0.64%, 0.65%, 0.66%, 0.67%, 0.68%, 0.69%, 0.70%, 0.71%, 0.72%, 0.73%, 0.74%, 0.75%, 0.76%, 0.77%, 0.78%, 0.79%, 0.80%, 0.81%, 0.82%, 0.83%, 0.84%, 0.85%, 0.86%, 0.87%, 0.88%, 0.89%, 0.90%, 0.91%, 0.92%, 0.93%, 0.94%, 0.95%, 0.96%, 0.97%, 0.98%, 0.99%, 1.00%, 1.10%, 1.20%, 1.30%, 1.40%, 1.50%, 1.60%, 1.70%, 1.80%, 1.90%, 2.00%, 2.10%, 2.20%, 2.30%, 2.40%, 2.50%, 2.60%, 2.70%, 2.80%, 2.90%, 3.00%, 3.10%, 3.20%, 3.30%, 3.40%, 3.50%, 3.60%, 3.70%, 3.80%, 3.90%, 4.00%, 4.10%, 4.20%, 4.30%, 4.40%, 4.50%, 4.60%, 4.70%, 4.80%, 4.90% and 4.99% (w/w).

It should further be appreciated that, preferably, compositions disclosed herein are substantially free of preservatives (i.e., preservatives not more than 0.01 wt %, and more typically not more than 0.005 wt %), or entirely free of preservatives. For example, preservatives that may not be included are benzalkonium chloride, cetrimide or cetrimonium chloride or bromide, benzododecinium bromide, miramine, cetylpyridinium chloride, polidronium chloride or polyquaternium-1, polyquaternium-42 (also known as polixetonium), sepazonium chloride; mercurial derivatives such as the phenylmercury salts (acetate, borate or nitrate), mercuriothiolate sodium (otherwise called thiomersal or thimerosal) and mercurobutol; amidines such as chlorhexidine digluconate or polyhexamethylene biguanide (PHMB); alcohols such as chlorobutanol or phenylethanol or benzyl alcohol or phenol or m-cresol or phenoxyethanol; parabens or esters such as parahydroxybenzoic acid, methylparaben, and propylparaben).

With respect to the sterilization of contemplated formulations it should be appreciated that contemplated formulations may be sterilized using all known manners of sterilization, including filtration through 0.22 micron filters, heat sterilization, autoclaving, radiation (e.g., gamma, electron beam, microwave). Advantageously, and as is shown in more detail below, the inventors have also discovered that contemplated formulations can be compounded from two batches in which the viscosity agent is separately sterilized using high-pressure saturated steam at 121° C. (for at least 5, or at least 10, or at least 15 minutes) from the ephedrine, buffer, and salt solution that was independently filter sterilized.

The pharmaceutical formulations disclosed herein are suitable for injectable use, such as, for example, intravenous, subcutaneous, intramuscular and intraperitoneal administration, and include sterile aqueous solutions and sterile powders for the extemporaneous preparation of sterile injectable solutions. The formulations can be sterile and can be fluid to the extent that easy syringability exists. They can be stable under the conditions of manufacture and storage and can be preserved against the contaminating action of microorganisms such as bacteria and fungi. The preventions of the action of microorganisms can be brought about by various antibacterial and antifungal agents, for example, parabens, chlorobutanol, phenol, benzyl alcohol, sorbic acid, and the like. Alternatively, the formulations can be preservative-free.

It may be preferable to include isotonic agents, for example, sugars or sodium chloride. Preferred osmolarity of the formulations is between 200-400 mOsmol/L, more preferably between 250-350 mOsmol/L.

Sterile injectable solutions may be prepared by incorporating the ephedrine, or pharmaceutically acceptable salt thereof, in the required amounts in the appropriate solvent with various of the other ingredients enumerated above, as required, followed by filter or terminal sterilization. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

Preferably the formulations may contain an excipient. Pharmaceutically acceptable excipients which may be included in the formulation include one or more pH adjusting agents (also referred to herein as pH adjusters) such as, but not limited to, alkaline pH adjusters such as sodium hydrogen carbonate, sodium carbonate, potassium hydroxide, sodium hydroxide, lithium hydroxide, magnesium hydroxide, calcium hydroxide, rubidium hydroxide, cesium hydroxide, strontium hydroxide and barium hydroxide; and/or acidic pH adjusters such as hydrochloric acid, sulfuric acid, adipic acid or a salt thereof, citric acid or a salt thereof, gluconic acid or a salt thereof, succinic acid or a salt thereof, ascorbic acid or a salt thereof, glacial acetic acid or a salt thereof, acetic acid or a salt thereof, tartaric acid or a salt thereof, fumaric acid or a salt thereof, maleic acid or a salt thereof, lactic acid or a salt thereof, malic acid or a salt thereof and phosphoric acid or a salt thereof. Preferably, the one or more pH adjusters comprises glacial acetic acid and/or sodium hydroxide.

Pharmaceutically acceptable excipients which also may be included in the formulation include buffers such as citrate buffer, phosphate buffer, acetate buffer, and bicarbonate buffer; amino acids; urea; alcohols; ascorbic acid; phospholipids; proteins, such as serum albumin, collagen, and gelatin; salts such as EDTA or EGTA, and sodium chloride; liposomes; polyvinylpyrrolidone; sugars, such as dextran, mannitol, sorbitol, and glycerol; propylene glycol and polyethylene glycol (e.g., PEG-4000, PEG-6000); glycerol; glycine; lipids; preservatives; suspending agents; stabilizers; and dyes. Non-limiting examples of stabilizers include antioxidants. Alternatively, the formulations can be preservative-free, stabilizer-free and/or dye-free.

The formulation also may contain a non-ionic detergent. Preferred non-ionic detergents include Polysorbate 20, Polysorbate 80, Triton X-100, Triton X-114, Nonidet P-40, Octyl α-glucoside, Octyl β-glucoside, Brij 35, Pluronic, and Tween 20. Alternatively, the formulations can be detergent-free.

The parenteral formulations may be sterilized. Non-limiting examples of sterilization techniques include filtration through a bacterial-retaining filter, terminal sterilization, incorporation of sterilizing agents, irradiation, and heating.

Administration of the above-described parenteral formulations may be by periodic injections of a bolus of the preparation, or may be administered by intravenous or intraperitoneal administration from a reservoir which is external (e.g., an intravenous bag) or internal (e.g., a bioerodable implant, a bioartificial or organ). See, e.g., U.S. Pat. Nos. 4,407,957 and 5,798,113, each incorporated herein by reference in their entireties. Intrapulmonary delivery methods and apparatus are described, for example, in U.S. Pat. Nos. 5,654,007, 5,780,014, and 5,814,607, each incorporated herein by reference in their entireties. Other useful parenteral delivery systems include ethylene-vinyl acetate copolymer particles, osmotic pumps, implantable infusion systems, pump delivery, encapsulated cell delivery, liposomal delivery, needle-delivered injection, needle-less injection, nebulizer, aeorosolizer, electroporation, and transdermal patch. Needle-less injector devices are described in U.S. Pat. Nos. 5,879,327; 5,520,639; 5,846,233 and 5,704,911, the specifications of which are herein incorporated herein by reference in their entireties. Any of the formulations described herein can be administered in these methods.

In certain embodiments, the premixed ephedrine composition is a liquid comprising ephedrine, or a pharmaceutically acceptable salt thereof, at a concentration of between about 2.5 mg/mL and about 20 mg/mL, preferably about 5 mg/mL to about 10 mg/mL. The premixed ephedrine composition may be a liquid comprising ephedrine, or a pharmaceutically acceptable salt thereof, at a concentration of about 5 mg/mL, about 6 mg/mL, about 7 mg/mL, about 8 mg/mL, about 9 mg/mL, or about 10 mg/mL.

The premixed ephedrine composition may be a liquid comprising ephedrine, or a pharmaceutically acceptable salt thereof, at a dose of between about 5 mg and about 10 mg, preferably about 5 mg, about 6 mg, about 7 mg, about 8 mg, about 9 mg, or about 10 mg.

Optionally, the premixed ephedrine composition comprises sodium chloride (preferably at concentrations of 0.9% or 0.45%), Ringer's lactate, or dextrose (preferably at 5% concentration) solution.

In other embodiments, the premixed ephedrine composition comprises ephedrine, or pharmaceutically acceptable salt thereof, at a concentration of about 5 mg/mL, sodium chloride at a concentration of about 9 mg/mL, water and one or more pH adjusters in an amount to render the initial pH of the composition to the range of 4.5 to 5.0.

In certain embodiments, the premixed ephedrine composition is disposed in a container or vessel that can maintain the sterility of, or prevent the contamination of, a premixed ephedrine composition. In certain embodiments, the container or vessel is a sealed container or vessel.

In certain embodiments, the ephedrine composition is disposed in a container or vessel and is formulated as a premixture.

In certain embodiments, the premixed ephedrine composition is disposed in a container or vessel and is formulated as a single use dosage. In certain, the premixed ephedrine composition is disposed in a container or vessel and is formulated as a dosage for multiple use.

In certain embodiments, the container or vessel includes, but is not limited to, glass vials (for example, but not limited to, flint glass vials), ampoules, plastic flexible containers, for example, but not limited to, polyvinyl chloride containers, VisIV™ plastic containers (Hospira, Inc., Lake Forest, Ill.), and CR3 elastomer copolyester ether containers (Hospira, Inc., Lake Forest, Ill.), CZ resin containers, polypropylene containers and syringes.

In certain embodiments, the headspace may be purged with an inert gas, such as nitrogen, argon or carbon dioxide. Preferably, if purging is done, the inert gas comprises nitrogen.

In certain embodiments, the premixed ephedrine composition can be stored as a liquid in an aliquot having a total volume of between about 1 mL to 100 mL, preferably about 5 mL to 10 mL.

In certain embodiments, the ephedrine composition comprises water, ephedrine, or a pharmaceutically acceptable salt thereof, and one or more pH adjusters, wherein initial pH is in the range of 4.5 to 5.0, and the product is pH stable for at least 6 months, preferably at least 12 months, more preferably at least 18 months, and most preferably at least 24 months, at 25±2° C. and 60±5% relative humidity. Preferably, the one or more pH adjusters comprises glacial acetic acid and/or sodium hydroxide. The composition may further comprise sodium chloride, Ringer's lactate, or dextrose, preferably sodium chloride.

The formulations may be used for the treatment of clinically important hypotension in the setting of anesthesia. The preferred dose is an initial dose of 5 to 10 mg, and additional doses may be administered in increments of 5 to 10 mg as needed, preferably not to exceed a total dosage of 50 mg. The formulation is preferably administered as an intravenous bolus.

As already indicated, the compositions disclosed herein can optionally further comprise a pharmacologically acceptable tonicity agent in addition to the chelating agent. As used herein, the term "tonicity agent" refers to an excipient capable of adjusting the osmotic pressure of a liquid antibody formulation. In some embodiments, the tonicity agent adjusts the osmotic pressure of the liquid antibody formulation to be isotonic, making the antibody formulation biologically compatible with the cells of the subject's body tissue. In yet another embodiment, a "tonicity agent" can contribute to improving the stability of all anti-CTLA-4 antibodies described herein. An "isotonic" formulation is a composition that has substantially the same osmotic pressure as human blood. Isotonic formulations generally have an osmotic pressure of about 250-350 mOsm. The term "hypotonic" is used to describe a formulation that has a lower osmotic pressure than human blood, while the term "hypertonic" describes a formulation that has a higher osmotic pressure than human blood. Used for. Isotonicity can be measured using, for example, a vapor pressure or freezing point type osmometer.

The tonicity agent used in preparing the compositions can exist in various forms. Tonicity agents are, for example, enantiomeric forms (eg L-enantiomers or D-enantiomers), or racemic forms; isomers (eg α or β, including act, ββ, αβ, βα)); Free acid or free base form; hydrate form (eg monohydrate); anhydride form.

In one embodiment, the tonicity agent is a saccharide. As used herein, the term "saccharide" refers to a group of molecules that are derivatives of polyhydric alcohols. Saccharides are commonly referred to as carbohydrates and can contain different amounts of sugar units (eg monosaccharides, disaccharides, polysaccharides). Saccharides suitable for use as tonicity agents include fructose, glucose, mannose, sorbose, xylose, lactose, maltose, sucrose, dextran, pullulan, dextrin, cyclodextrin, soluble starch, hydroxyethyl starch, water soluble glucan, And saccharides selected from the group consisting of these mixtures.

In another embodiment, the tonicity agent is a polyol. In this specification, the term "polyol" means an excipient having a large number of hydroxyl groups, such as sugar (reducing sugar, non-reducing sugar), sugar alcohol, sugar acid and the like. In one embodiment, the polyol has a molecular weight of less than about 600 kD (eg, in the range of about 120 to about 400 kD). "Reducing sugar" means a sugar containing a hemiacetal group that can reduce metal ions or covalently react with lysine and other amino groups in proteins. "Non-reducing sugar" means a sugar that does not have this property of reducing sugar. Polyols suitable for use as tonicity agents include those in the group consisting of mannitol, trehalose, sorbitol, erythritol, isomalt, lactitol, maltitol, xylitol, glycerol, propylene glycol, polyethylene glycol, inositol, and mixtures thereof. The polyol selected from is mentioned. In one embodiment, the tonicity agent is a non-reducing sugar selected from the group consisting of trehalose, sucrose, and mixtures thereof.

In one embodiment, the tonicity agent is mannitol. In another embodiment, the tonicity agent is D-mannitol. In another embodiment, the tonicity agent is trehalose. In another embodiment, the tonicity agent is aa-trehalose dihydrate. In another embodiment, the tonicity agent is sucrose.

In one embodiment, the concentration of the tonicity agent in the liquid pharmaceutical composition ranges from about 1 mmol to about 600 mmol, from about 1 mmol to about 400 mmol, from about 1 mmol to about 300 mmol, from about 200 mmol to about 275 mmol. is there. In another embodiment, the tonicity agent is mannitol and is present in the liquid pharmaceutical composition at a concentration of about 247 millimolar. In another embodiment, the tonicity agent is trehalose and is present in the liquid pharmaceutical composition at a concentration of about 222 millimolar. In another embodiment, the tonicity agent is trehalose and is present in the liquid pharmaceutical composition at a concentration of about 238 mmol. In another embodiment, the tonicity agent is sucrose and is present in the liquid pharmaceutical composition at a concentration of about 263 millimolar.

In one embodiment, the concentration of tonicity agent in the liquid pharmaceutical composition ranges from about 1 mg/ml to about 300 mg/ml, from about 1 mg/ml to about 200 mg/ml, from about 50 mg/ml to about 150 mg/ml. In another embodiment, the tonicity agent is mannitol and is present in the liquid pharmaceutical composition at a concentration of about 45 mg/ml. In another embodiment, the tonicity agent is trehalose and is present in the liquid pharmaceutical composition at a concentration of about 84 mg/ml. In another embodiment, the tonicity agent is trehalose and is present in the liquid pharmaceutical composition at a concentration of about 90 mg/ml. In another embodiment, the tonicity agent is sucrose and is present in the liquid pharmaceutical composition at a concentration of about 90 mg/ml.

In one embodiment, the tonicity agent is a salt (eg, sodium chloride). In one embodiment, when the tonicity agent is a salt, the concentration of that salt in the liquid pharmaceutical composition is from about 1 mg/ml to about 20 mg/ml. In another embodiment, the tonicity agent is sodium chloride and the concentration of sodium chloride in the liquid pharmaceutical composition is about 8.18 mg/ml.

Intermediate ranges of the above concentrations for tonicity agents are also part of this disclosure. For example, a range using a combination of any of the above values as the upper limit and/or the lower limit is also included in the present disclosure.

Intermediate ranges of the above concentrations for tonicity agents are also part of this disclosure. For example, a range using a combination of any of the above values as the upper limit and/or the lower limit is also included.

The present disclosure is also directed to a kit for using and administering an injectable formulation at room temperature, comprising: an ephedrine formulation having 4 mg/mL to 6 mg/mL of ephedrine, a pH adjuster and water;

wherein the initial adjusted pH of the formulation is between 4.5 and 5.0; and wherein the pH drift of the formulation is less than 0.5 after storage over at least two months at 25° C. and 60% relative humidity. The kit is an assemblage of materials or components, including at least one of the inventive compositions or formulations.

The ephedrine formulation in the kit may be present in a glass vial or a polypropylene syringe. The polypropylene syringe preferably includes graduations thereon, the graduations being volume based and being indicative of the amount of ephedrine formulation being administered to a patient from the syringe.

Instructions for use may be included in the kit. "Instructions for use" typically include a tangible expression describing the technique to be employed in using the components of the kit to affect a desired outcome. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example, the components can be provided at room, refrigerated or frozen temperatures. The components of the kit as disclosed herein are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. As used herein, the term "package" refers to a suitable solid matrix or material such as glass, plastic, paper, foil, and the like, capable of holding the individual kit components. The packaging material generally has an external label which indicates the contents and/or purpose of the kit and/or its components.

The following examples are provided for illustrative purposes only and should not be interpreted as limiting the present disclosure.

EXAMPLES

The following examples illustrate some of the experiments leading to the formulations according to the inventive subject matter, however, should not be construed to limit the scope of the claims in any way.

One example of a formulation disclosed herein is shown in Table 1 below:

TABLE 1

| Ingredient | Grade | Qty/mL |
|---|---|---|
| Ephedrine Sulfate | USP | 5 mg |
| Sodium Chloride | USP | 9 mg |
| Glacial Acetic Acid/Sodium Hydroxide | NF | q.s. for pH adjustment |
| Water for injection | USP | q.s. |

Stability studies for inventive formulations are illustrated in tables 2 and 3 below. As can be seen from these tables, the pH drift is minimal for the formulations disclosed herein.

TABLE 2

| | NVK014 at pH 4.5 Lot: 10690 | | | | | | | | |
|---|---|---|---|---|---|---|---|---|---|
| | | Accelerated Stability (40° C. ± 2° C./75% RH ± 5% RH) | | | | | Long-Term Stability (25° C. ± 2° C./60% RH ± 5% RH) | | |
| Test Parameter | Initial | 1 month | 2 months | 3 months | 6 months | 1 month | 2 months | 3 months | 6 months |
| Appearance | Clear, colorless solution | Clear, colorless solution | Clear, colorless solution | Clear, colorless solution | Clear, colorless solution | Clear, colorless solution | Clear, colorless solution | Clear, colorless solution | Clear, colorless solution |
| pH | 4.58 | 4.60 | 4.87 | 4.90 | 4.93 | 4.58 | 4.87 | 4.90 | 4.93 |
| Assay of Ephedrine Sulfate (%) | 98.91 | 101.05 | 99.23 | 99.65 | 102.39 | 101.99 | 99.15 | 99.38 | 102.40 |
| Related Norephedrine Compounds (%) | 0.08 | 0.08 | 0.08 | 0.08 | 0.08 | 0.08 | 0.08 | 0.08 | 0.08 |

TABLE 3

| | | NVK014- 5 ml PTS presentation; Lot: 11715 | | | | |
|---|---|---|---|---|---|---|
| | | | Accelerated Stability (40° C. ± 2° C./75% RH ± 5% RH) | | | |
| Test Parameter | | Initial | 1 month | 2 months | 3 months | 6 months |
| Appearance | | Clear, colorless solution | Clear, colorless solution | Clear, colorless solution | Clear, colorless solution | Clear, colorless solution |
| pH | | 4.8 | 5.2 | 5.2 | 5.0 | 5.22 |
| Osmolality (mOsm/kg) | | 312 | NT | NT | 315 | 318 |
| Particulate matter | ≥10 um | 2 | NT | NT | 8 | 6 |
| | ≥25 um | 0 | | | 0 | 0 |
| Syringe functionality tests | Break loose force (N) | 14 | 12 | 7 | 3 | 8 |
| | Glide force (N) | 7 | 7 | 7 | 7 | 7 |

TABLE 3-continued

| | | | | | | |
|---|---|---|---|---|---|---|
| Assay of Ephedrine Sulfate (%) | | 99.9 | 99.5 | 99.0 | 98.6 | 101.5 |
| Enantiomeric purity (d-EPH) (%) | | NT | 0.03 | 0.03 | 0.04 | 0.03 |
| Related Compounds (%) | Norephedrine | ND | ND | ND | ND | ND |
| | Unknown (RRT) | 0.06$_{(0.81)}$ | 0.07$_{(0.81)}$ | 0.07$_{(0.81)}$ | 0.08$_{(0.81)}$ | 0.08$_{(0.81)}$ |
| | | | | | | 0.08$_{(1.37)}$ |
| | Total | 0.06 | 0.07 | 0.07 | 0.08 | 0.14 |

NVK014- 5 ml PTS presentation; Lot: 11715
Long-Term Stability
(25° C. ± 2° C./60% RH ± 5% RH)

| | Test Parameter | 1 month | 2 months | 3 months | 6 months |
|---|---|---|---|---|---|
| | Appearance | Clear, colorless solution | Clear, colorless solution | Clear, colorless solution | Clear, colorless solution |
| | pH | 5.0 | 5.1 | 4.77 | 5.35 |
| | Osmolality (mOsm/kg) | NT | NT | 315 | 313 |
| Particulate matter | ≥10 um | NT | NT | 6 | 4 |
| | ≥25 um | | | 0 | 0 |
| Syringe functionality tests | Break loose force (N) | 8 | 9 | 11 | 8 |
| | Glide force (N) | 7 | 7 | 7 | 7 |
| Assay of Ephedrine Sulfate (%) | | 99.0 | 99.6 | 99.0 | 101.4 |
| Enantiomeric purity (d-EPH) (%) | | 0.04 | 0.04 | 0.04 | 0.03 |
| Related Compounds (%) | Norephedrine | ND | ND | ND | |
| | Unknown (RRT) | 0.07$_{(0.81)}$ | 0.08$_{(0.81)}$ | 0.08$_{(0.81)}$ | 0.08$_{(0.81)}$ |
| | Total | 0.07 | 0.08 | 0.08 | 0.08 |

Comparative Examples—stability studies: to compare the stability of the instantly disclosed formulations to those currently available, the inventors have done a comparative study, the results of which are seen in the tables below. The Table 4 (below) is shows that if the initial pH of Ephedrine Sulfate Injection, 5 mg/mL is adjusted to a pH >4.8, in this case 5.14-5.20, then the pH of the drug product solution goes outside of the recommended pH range (4.5-7.0) in the drug product USP monograph. It is noted that currently available Ephedrine, that is the reference listed drug (RLD), is available as a concentrate, Ephedrine Sulfate Injection, 50 mg/mL with a pH of around 5.1 to 5.3. However, to administer the drug to patients, the RLD must be diluted to a concentration of 5 mg/mL. The inventors of this disclosure unexpectedly developed a ready-to-use formulation (Ephedrine Sulfate Injection, 5 mg/mL) which is stable at room temperature up to 24 months or more, where in the pH of the solution remains within the recommended pH range of the USP drug product monograph throughout the shelf-life. In one embodiment, the inventors have found that, when the pH of the formulation is set to 4.5-4.8, it results in a long shelf life without any pH drift. In another embodiment, the inventors found that if the pH of the formulation is greater than 4.8, a drift in pH is possible, and the pH may go over 7.0 within the proposed shelf-life, as seen in Table 4.

TABLE 4

| | NVK014- A (Without Nitrogen purging in the headspace) | | | | | | |
|---|---|---|---|---|---|---|---|
| | | Accelerated Stability (40° C. ± 2° C./75% RH ± 5% RH) | | | Long-Term Stability (25° C. ± 2° C./60%RH ± 5% RH) | | |
| Test Parameter | Initial | 1 month | 2 months | 3 months | 1 month | 2 months | 3 months |
| Appearance | Clear, colorless solution | Clear, colorless solution | Clear, colorless solution | Clear, colorless solution | Clear, colorless solution | Clear, colorless solution | Clear, colorless solution |
| pH | 5.14 | 6.97 | 6.48 | 6.68 | 7.24 | 6.50 | 6.65 |
| Assay of Ephedrine Sulfate (%) | 99.82 | 101.59 | 99.91 | 99.49 | 100.35 | 100.08 | 98.81 |
| Related Compounds (%) Norephedrine | 0.08 | 0.08 | 0.08 | 0.08 | 0.08 | 0.08 | 0.08 |

Table 5 evaluates the effect of oxygen in the headspace. The inventors have found that the headspace oxygen does not impact the drug product.

Table 2 (also described earlier) evaluates the stability of the drug product at or around the lower end of the pH, which is 4.5. The inventors surprisingly found that the change in

TABLE 5

| | NVK014- B (Purged with Nitrogen in the headspace) | | | | | | |
|---|---|---|---|---|---|---|---|
| | | Accelerated Stability (40° C. ± 2° C./75% RH ± 5% RH) | | | Long-Term Stability (25° C. ± 2° C./60% RH ± 5% RH) | | |
| Test Parameter | Initial | 1 month | 2 months | 3 months | 1 month | 2 months | 3 months |
| Appearance | Clear, colorless solution | Clear, colorless solution | Clear, colorless solution | Clear, colorless solution | Clear, colorless solution | Clear, colorless solution | Clear, colorless solution |
| pH | 5.14 | 6.63 | 6.66 | 6.69 | 6.66 | 6.42 | 6.61 |
| Assay of Ephedrine Sulfate (%) | 99.82 | 100.61 | 99.93 | 99.46 | 100.68 | 99.66 | 99.01 |
| Related Compounds (%) Norephedrine | 0.1 | 0.1 | 0.1 | 0.08 | 0.1 | 0.1 | 0.08 |

TABLE 6

| | NVK014 at pH 7.0 Lot: 10691 | | | | | | | | |
|---|---|---|---|---|---|---|---|---|---|
| | | Accelerated Stability (40° C. ± 2° C./75% RH ± 5% RH) | | | | Long-Term Stability (25° C. ± 2° C./60% RH ± 5% RH) | | | |
| Test Parameter | Initial | 1 month | 2 months | 3 months | 6 months | 1 month | 2 months | 3 months | 6 months |
| Appearance | Clear, colorless solution | Clear, colorless solution | Clear, colorless solution | Clear, colorless solution | Clear, colorless solution | Clear, colorless solution | Clear, colorless solution | Clear, colorless solution | Clear, colorless solution |
| pH | 6.7 | 6.9 | 7.1 | 7.1 | 7.3 | 6.9 | 7.0 | 7.1 | 7.3 |
| Assay of Ephedrine Sulfate (%) | 99.48 | 100.91 | 100.62 | 100.75 | 102.14 | 100.66 | 100.60 | 100.16 | 101.78 |
| Related Compounds (%) Norephedrine | 0.08 | 0.08 | 0.08 | 0.08 | 0.08 | 0.08 | 0.08 | 0.08 | 0.08 |

Table 6 (above) evaluates the stability of the drug product at or around a pH of 7.0 (the higher end of the USP range). Although, chemically, the drug product was found to be stable, the pH was found to go beyond 7.0.

Table 7 (below) provides additional stability data, illustrating the stability of the formulation disclosed herein, for up to 12-months at long-term storage condition of (25° C./60% RH).

pH when the drug product solution was set at a pH between 4.5-4.8, was less than 1 unit within the period it was evaluated. This observation led to the realization that to achieve a product within the USP recommended pH range throughout the proposed shelf-life, it was critical to set the pH of the instantly disclosed ready-to-use formulation (Ephedrine Sulfate Injection, 5 mg/mL) on the lower end of the range. This was also proven based on the buffer capacity

TABLE 7

| | NVK014- Ephedrine Sulfate Injection, USP 5 mg/mL | | | | |
|---|---|---|---|---|---|
| | Long-term storage conditions (25° C. ± 2° C./60% RH ± 5% RH) | | | | |
| Test Parameter | Initial | 3 months | 6 months | 9 months | 12 months |
| Appearance | Clear, colorless solution | Clear, colorless solution | Clear, colorless solution | Clear, colorless solution | Clear, colorless solution |
| pH | 5.1 | 5.1 | 5.1 | 5.2 | 4.9 |
| Osmolality (mOsm/kg) | 313 | 315 | 314 | NT | 316 |
| Assay of Ephedrine Sulfate (%) | 100.3 | 101.0 | 101.0 | 100.0 | 100.1 |
| Related Compounds (%) Norephedrine | 0.0 | 0.0 | 0.0 | 0.0 | ND |
| Related Compounds (%) Pseudoephedrine | ND | ND | ND | ND | ND |
| Related Compounds (%) Phenylacetylcarbinol | ND | ND | ND | ND | ND |
| Related Compounds (%) Any unspecified impurity | 0.0 | ND | ND | ND | ND |
| Total | 0.0 | 0.0 | 0.00 | 0.0 | 0.0 | acetic acid provides at the lower end of the recommended pH range (See data table below). The higher buffer capacity at lower end of the pH is imparted by acetic acid because the pH of the solution is closer or equal to the pKa of acetic acid (4.76).

TABLE 8

| Lot # | Adjusted pH | 0.1N NaOH consumed to change the pH by 1 unit | Final pH |
|---|---|---|---|
| 11029; Sub-lot A | 4.63 | 110 uL | 5.66 |
| 11029; Sub-lot B | 5.07 | 40 uL | 6.06 |

In one embodiment, the inventors have found that the type of container used for making and/or storing the compositions and formulations disclosed herein may be important for the stability of the composition or formulation. As can be seen from Table 9, polypropylene vial and C-C system provides the best pH stability, having the least drift.

In one embodiment, the proposed container-closure (C-C) system comprises a 10 mL USP Type-I clear glass vial with a suitable bromobutyl stopper and a suitable flip-off cap.

TABLE 9

Lot #: 11126
pH of the bulk solution in glass vessel = 4.8
pH in different containers after 24 hours

| Proposed C-C system | 4.93 |
|---|---|
| Scintillation vial | 6.98 |
| Polypropylene vial | 4.80 |

Comparative Examples using different container systems, and stability at different pH is shown in tables 10 and 11 respectively.

TABLE 10

Lot #: 10603
pH of the bulk solution in glass vessel = 5.14
pH in different containers after 24 hours

| Proposed C-C system | 5.56 |
|---|---|
| Scintillation vial | 6.91 |
| Polypropylene vial | 5.26 |

TABLE 11

Lot #: 10847
pH of the bulk solution in glass vessel = 5.50
pH in different containers after 24 hours

| Proposed C-C system | 6.12 |
|---|---|
| Scintillation vial | 6.82 |
| Polypropylene vial | 5.72 |

The test methods for assay of Ephedrine and determination of organic impurities in Ephedrine Sulfate Injection USP are based on High Performance Liquid Chromatography (HPLC) with ultraviolet (UV) absorption detection. Both methods utilize the same chromatographic system, which includes isocratic elution and a narrow-bore column with 2.6-μm packing L11 but differ in standard and sample solution concentrations. The mobile phase is a 1:99 mixture of acetonitrile and aqueous buffer containing triethylamine and phosphoric acid, pH 4.0. The HPLC-UV method from the United States Pharmacopoeia (USP) monograph utilized showed several related compounds eluted and no mass balance was achieved for a drug solution sample degraded under oxidative conditions. Therefore, additional method evaluation and development was performed, which resulted in a method for assay and related compounds (both unspecified and specified) that can detect the stereoisomers in the drug product, a critical distinction to have to detect the content of the pharmacologically active and/or non-active isomer. An analytical method with tighter system precision and no peaks interferences in the chromatograms with Ephedrine and the three specified impurities (Pseudoephedrine, Norephedrine and L-Phenylacetylcarbinol) was developed and optimized. A snapshot of the chromatographic conditions is illustrated in Table 12 below:

TABLE 12

| HPLC | Waters Alliance e2695 or equivalent |
|---|---|
| Column | Hypersil Phenyl-2, 4.8 × 250 nm, 5 μm |
| Column Temperature | 25° C. |
| Sample Temperature | Ambient |
| Injection volume | 20.0 μL |
| Flow Rate | 1.0 mL/min |
| Detection | Spectrum: 200-400 nm, resolution 1.2 nm<br>Single channel: 206 nm, resolution 4.8 nm<br>Sampling rate: 5 Hz,<br>Filter Time Constant: Slow (optional) |
| Mobile Phase | TEA-OPA Buffer/Acetonitrile/Methanol (900:50:50 v/v/v)<br>Isocratic elution |
| Run Time | 30 min |

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

In some embodiments, the numbers expressing quantities of ingredients, properties such as concentration, reaction conditions, and so forth, used to describe and claim certain embodiments of the disclosure are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the disclosure may contain certain errors necessarily resulting from the standard deviation found in their respective testing measurements.

It should be apparent, however, to those skilled in the art that many more modifications besides those already described are possible without departing from the inventive concepts herein. The inventive subject matter, therefore, is not to be restricted except in the spirit of the disclosure. One skilled in the art will recognize many methods and materials similar or equivalent to those described herein, which could be used in the practice of the present invention. Indeed, the present invention is in no way limited to the methods and materials described.

Moreover, in interpreting the disclosure all terms should be interpreted in the broadest possible manner consistent with the context. In particular the terms "comprises" and "comprising" should be interpreted as referring to the elements, components, or steps in a non-exclusive manner, indicating that the referenced elements, components, or steps can be present, or utilized, or combined with other elements, components, or steps that are not expressly referenced.

What is claimed is:

1. A method of treating hypotension in a subject in need thereof, comprising:
    administering to the subject a storage-stable and sterile ephedrine composition from a pre-filled syringe;
    wherein the ephedrine composition comprises about 5 mg/mL of ephedrine or a pharmaceutically acceptable salt thereof; about 9 mg/mL of sodium chloride; a pH adjuster comprising acetic acid; and water;
    wherein the initial adjusted pH of the composition is in the range of about 4.6 to 4.8;
    wherein the pH drift of the composition is less than 0.5 after storage for 6 months at 25° C. and 60% relative humidity; and
    wherein the composition contains about 5% or less total impurities after storage for 6 months at 25° C. and 60% relative humidity as determined by HPLC.

2. The method of claim 1, further comprising a step of sterilizing the ephedrine composition.

3. The method of claim 2, wherein the step of sterilizing comprises filter sterilization.

4. The method of claim 2, wherein the step of sterilizing comprises autoclaving.

5. The method of claim 1, further comprising a step of filling the ephedrine composition into a syringe.

6. The method of claim 1, further comprising a step of filling the ephedrine composition into a syringe in an amount of between about 5 mL to about 100 mL.

7. The method of claim 1, further comprising a step of filling the ephedrine composition into a syringe in an amount of about 1 mL, about 5 mL, about 10 mL, about 20 mL, about 50 mL, or about 100 mL.

8. The method of claim 1, wherein the salt of the ephedrine is ephedrine sulfate.

9. The method of claim 1, wherein the ephedrine composition comprises ephedrine sulfate at a concentration of about 5 mg/mL.

10. The method of claim 1, wherein the pre-filled syringe is manufactured from a polymer.

11. The method of claim 1, wherein the pre-filled syringe contains between about 1-2 mL of the ephedrine composition.

12. The method of claim 1, wherein the pre-filled syringe contains between about 1-10 mL of the ephedrine composition.

13. The method of claim 1, wherein the pH adjuster is present in an amount sufficient to adjust the pH of the ephedrine sulfate composition to pH 4.6 to 4.8.

14. The method of claim 1, wherein the storage-stable and sterile ephedrine composition is substantially free of a preservative.

15. The method of claim 1, wherein the composition contains about 4 or less total impurities after storage for 6 months at 25° C. as determined by HPLC.

* * * * *